United States Patent [19]

Manzer et al.

[11] Patent Number: 5,026,930
[45] Date of Patent: * Jun. 25, 1991

[54] GAS-PHASE FLUORINATION PROCESS

[75] Inventors: Leo E. Manzer; V. N. Mallikarjuna Rao, both of Wilmington, Del.

[73] Assignee: E. I. Du Pont de Nemours and Company, Wilmington, Del.

[*] Notice: The portion of the term of this patent subsequent to Aug. 23, 2005 has been disclaimed.

[21] Appl. No.: 465,401

[22] Filed: Jan. 16, 1990

Related U.S. Application Data

[63] Continuation of Ser. No. 197,220, May 23, 1988, abandoned, which is a continuation-in-part of Ser. No. 85,027, Aug. 13, 1987, Pat. No. 4,766,259.

[51] Int. Cl.$^5$ .................... C07C 17/04; C07C 17/20; C07C 19/02
[52] U.S. Cl. .................... 570/168; 570/166
[58] Field of Search .................... 570/168, 166

[56] References Cited

U.S. PATENT DOCUMENTS

| | | | |
|---|---|---|---|
| 3,258,500 | 6/1966 | Swamer et al. | 260/653.7 |
| 3,755,477 | 8/1973 | Firth et al. | 260/653.4 |
| 4,766,259 | 9/1988 | Manzer et al. | 570/168 |

FOREIGN PATENT DOCUMENTS 1196345 11/1985 Canada.
1000483 8/1965 United Kingdom.

Primary Examiner—J. E. Evans
Attorney, Agent, or Firm—James E. Shipley

[57] ABSTRACT

An improved gas-phase process for the manufacture of 1,1-difluoro-1,2-dichloroethane and/or 1-fluoro-1,1,2-trichloroethane by contacting a suitable trihaloethylene and/or a tetrahaloethane with hydrogen fluoride in the presence of a metal in combination with a high fluorine content aluminum-containing compound, the reaction being preferably conducted under controlled conditions whereby the production of 1,1,1-trifluorochloroethane is minimized.

10 Claims, No Drawings

GAS-PHASE FLUORINATION PROCESS

This application is a continuation of application Ser. No. 07/197,220 filed May 23, 1988, now abandoned which is a continuation in part of Ser. No. 07/085,027 filed Aug. 13, 1987, now U.S. Pat. No. 4,766,259.

FIELD OF THE INVENTION

An improved process for the manufacture of 1,1-difluoro-1,2-dichloroethane, $CClF_2CH_2Cl$, and/or 1-fluoro-1,1,2-trichloroethane, $CCl_2FCH_2Cl$, more particularly, a gas-phase reaction of a suitable trihaloethylene, $CClX=CHCl$, wherein $X=Cl$ or $F$, and/or tetrahaloethane, $CCl_2XCH_2Cl$, wherein $X=Cl$ or $F$, with hydrogen fluoride in the presence of a selected metal in combination with a high fluorine content aluminum-containing compound, the reaction preferably being conducted under controlled conditions whereby the production of 1,1,1-trifluorochloroethane is minimized.

BACKGROUND OF THE INVENTION

U.S. Pat. No. 3,755,477 describes a process for producing fluorinated aliphatic hydrocarbons which comprises fluorinating a halogenated aliphatic hydrocarbon, including trichloroethylene, by reaction in the gas phase with hydrogen fluoride in the presence of a steam-treated and calcined chromium oxide catalyst prepared by a multi-step process. Example 22, col. 5, with trichloroethylene as a raw material, shows formation of $CF_3CH_2Cl$ at 6.2/1 $HF/C_2HCl_3$ mol ratio, 3.6 seconds contact time and 290° C. reaction temperature. In this example, the trifluorinated product is reported as the sole product evidently formed to the exclusion of the desired $CClF_2CH_2Cl$ product.

U.S. Pat. No. 3,258,500 describes a process for the catalytic vapor phase reaction of HF with various halohydrocarbons, including trichloroethylene, at 150° to 700° C. reaction temperatures in the presence of a catalyst that consists essentially of a heat-activated anhydrous chromium (III) oxide which may be supported on alumina. This catalyst is highly active. Although trichloroethylene is disclosed among the halogenated aliphatic hydrocarbons that may be employed, there is no example of its use as a raw material in the disclosed process. Examples 17 through 20, however, show use of other halo and polyhaloethylenes at 300° to 400° C.. In each case, the main reaction product is that wherein the halo groups other than fluoro originally present in the halo or polyhaloethylene have all been replaced by fluoro groups.

GB No. 1,000,485 describes a process for the preparation of organic fluorinated compounds by fluorination of halo-olefins in the gaseous phase and at a temperature preferably within the range 200° to 400° C.. The catalyst consists essentially of partially fluorinated alumina impregnated with one or more polyvalent metal halides. The polyvalent metal may be chromium, cobalt, nickel, or manganese. The total content of polyvalent metal halide expressed as oxide is not more than 15% by weight of the partially fluorinated (70–80%) alumina expressed as alumina. Example 1 (Table 1) shows reaction of trichloroethylene with HF over such catalyst yields $CF_3CH_2Cl$ as the major product with $CClF_2CH_2Cl$ as a very minor product at 280° to 360° C. In addition, the patent states that if fluorination of the catalyst is excessive, the activity of the catalyst is impaired (page 3, column 2, lines 85–87).

The references do not show how to produce selectively both 1,1-difluoro-1,2-dichloroethane and 1-fluoro-1,1,2-trichloroethane while minimizing the production of 1,1,1-trifluorochloroethane.

The process of the instant invention achieves the desired high degree of selectivity by minimizing the formation of the trifluorochloroethane, through catalyst selection and control of the reaction variables as discussed below and illustrated in the Examples.

SUMMARY OF THE INVENTION

What has been discovered is a process for the preparation of 1,1-difluoro-1,2-dichloroethane and/or 1-fluoro-1,1,2-trichloroethane by fluorination of a trihaloethylene, $CClX=CHCl$, wherein $X=Cl$ or $F$, and/or tetrahaloethane, $CCl_2XCH_2Cl$, wherein $X=Cl$ or $F$, which process comprises contacting in the gaseous phase at about 100° to about 200° C. said trihaloethylene and/or tetrahaloethane with HF and a catalyst composition comprising a catalytically effective amount of at least one metal in an oxidation state greater than zero, said metal selected from the group consisting of iron, manganese, magnesium, and nickel, said metal in combination with an aluminum-containing compound consisting essentially of aluminum and fluorine in such proportions that the fluorine content corresponds to an $AlF_3$ content of at least 90% by weight of the catalyst composition exclusive of the metal, said $AlF_3$ content being obtained by pretreatment of the unfluorinated catalyst composition with a vaporizable fluorine-containing compound, said contacting step producing a product stream containing 1,1-difluoro-1,2-dichloroethane and/or 1-fluoro-1,1,2-trichloroethane, and, thereafter, separating the 1,1-difluoro-1,2-dichloroethane and/or 1-fluoro-1,1,2-trichloroethane from the product stream.

DETAILS OF THE INVENTION

The trihaloethylene of this invention defined by the formula, $CClX=CHCl$, wherein $X=Cl$ or $F$, and includes $CCl_2=CHCl$ and $CClF=CHCl$, and mixtures of these. The tetrahaloethane is defined by the formula $CCl_2XCH_2Cl$, wherein $X=Cl$ or $F$, and includes $CCl_3CH_2Cl$ and $CCl_2FCH_2Cl$, and mixtures thereof. Of all these raw materials, trichloroethylene is preferred.

By a high fluorine content aluminum-containing compound is meant a composition comprising aluminum and fluorine in such proportions that the total fluorine content of the catalyst composition taken as $AlF_3$ corresponds to at least 90 weight percent, exclusive of the metal, i.e., iron, manganese, nickel or magnesium, preferably 95 weight percent $AlF_3$ or more. The remainder of the composition may include alumina or aluminum oxyfluoride.

The invention catalyst composition can be prepared in any manner known to the art. For example, the invention catalyst composition can be prepared by fluorination of alumina impregnated with a solution of at least one iron, manganese, nickel, or magnesium compound which may be in the form of the oxide, oxyhalide, halide, pseudohalide, nitrate, sulfate or other compound of the metal convertible to the fluoride or oxyfluoride under the conditions of the HF pretreatment step described herein. The halides include fluorides, chlorides and bromides. The pseudohalides include cyanides, cyanates and thiocyanates. The preferred metal is manganese.

In addition, the invention catalyst composition can also be prepared by co-precipitation of the catalytic metal and the aluminum as the hydroxides which are thereafter dried and calcined to form the mixed oxides, a technique well known to the art. The resulting oxide is then pretreated with HF as described herein.

The total content of iron, manganese, nickel, or magnesium expressed as the divalent oxide is not more than 50% by weight of the catalyst composition and preferably not more than 20% by weight of the catalyst composition, and usually at least 0.02% by weight of the catalyst composition. A more preferred range is 0.1 to 10% by weight of the catalyst composition.

The unfluorinated catalyst composition can be fluorinated to the desired fluoride content by treating with a fluorine-containing compound at elevated temperatures, e.g., at about 200° to about 450° C.. The pretreatment with a vaporizable fluorine-containing compound such as HF, $SF_4$, $CCl_3F$, $CCl_2F_2$, $CHF_3$ or $CCl_2FCClF_2$ can be done in any convenient manner including in the reactor which is to be used for contacting the trihaloethylene and/or tetrahaloethane with HF. By vaporizable fluorine-containing compound is meant a fluorine containing compound which, when passed over the catalyst of the instant invention at the indicated conditions, will fluorinate the catalyst to the desired degree.

A suitable catalyst may be prepared, for example, as follows:

A quantity of $Al_2O_3$ is impregnated with a solution, usually aqueous, of a catalytically effective amount of one or more of the metal compounds described above. By catalytically effective amount is meant an amount of the metal which causes the production of the desired compounds in the process of the instant invention. Normally, this amount, expressed as the divalent oxide, will be between about 0.02 to 50 weight percent of the alumina support, preferably not more than 20 weight percent, and more preferably 0.1 to 10 weight percent. The impregnated $Al_2O_3$ can be dried until essentially all moisture is removed, e.g., for about 18 hours at about 300° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and HF, or other vaporizable fluorine containing compounds such as $SF_4$, $CCl_3F$, $CCl_2F_2$, $CHF_3$ or $CCl_2FCClF_2$, diluted with $N_2$ is passed through the reactor. The $N_2$ can be gradually reduced until only HF, or other vaporizable fluorine containing compounds such as $SF_4$, $CCl_3F$, $CCl_2F_2$, $CHF_3$ or $CCl_2FCClF_2$, is being passed through the reactor. At this point the temperature can be increased to about 450° C. and held at that temperature to convert the impregnated $Al_2O_3$ to a fluoride content corresponding to at least 90% $AlF_3$ by weight, e.g., for 15 to 300 minutes, depending on the flow of the fluorine containing compound and the catalyst volume.

Another suitable procedure for catalyst preparation is to add an aqueous solution of ammomium hydroxide to a solution of $Al(NO_3)_3$ and one or more of the metals described above in the form of a water soluble compound, such as $Mg(NO_3)_2$. During the addition of the nitrate solution, the pH is maintained at 8.8. At the end of the addition, the solution is filtered, the white solid obtained is washed with water, dried and slowly heated to 500° C., where it is calcined. The calcined product is then treated with suitable fluorine containing compound as described above.

The reaction of the trihaloethylene and/or tetrahaloethane with HF in the presence of the catalyst of the instant invention is conducted at about 100° to 200° C., preferably about 100° to 180° C., and most preferably about 120° to 160° C., with a contact time of about 2 to about 80 seconds, preferably about 3 to about 60 seconds.

The molar ratio of HF to the trihaloethylene and/or tetrahaloethane can range from about 0.5/1 to about 15/1, preferably about 1/1 to 10/1, and more preferably about 2/1 to 5/1.

In general, with a given catalyst composition, the higher the temperature, the greater the HF/trihaloethylene and/or tetrahaloethane mol ratio, and the longer the contact time, the greater is the conversion to fluorinated products and the greater is the production of polyfluorinated products. The above variables can be balanced, one against the other, so that formation of $CClF_2CH_2Cl$ and/or $CCl_2FCH_2Cl$ is maximized and formation of the more highly fluorinated $CF_3CH_2Cl$ is minimized.

A key feature of the invention is that through catalyst selection and process control as described herein the desired di- and mono-fluorinated products can be obtained as the major products. Preferably, the reaction variables are controlled so as to keep the production of the trifluoro product below about 10 area percent of the products produced, as determined gas chomatographically. Thus, as illustrated in the Examples with trichloroethylene, the mono- and di-fluorinated products are obtained in very high yields while minimizing the production of the tri-fluorinated product.

During the course of the reaction, unreacted starting materials and underfluorinated products can be recycled.

The reaction of the trihaloethylene and/or tetrahaloethane with HF may be conducted in any suitable reactor, including fixed and fluidized bed reactors. The reaction vessel should be constructed from materials which are resistant to the corrosive effects of hydrogen fluoride such as Hastelloy and Inconel.

Pressure is not critical. Atmospheric and superatmospheric pressures are the most convenient and are therefore preferred.

$CClF_2CH_2Cl$ produced by the invention has utility as a solvent in electronic applications. $CCl_2FCH_2Cl$ has utility as a degreasing solvent. Both $CClF_2CH_2Cl$ and $CCl_2FCH_2Cl$ can also be used as starting materials for the preparation of other useful compounds, e.g., 1,1,1,2-tetrafluoroethane.

EXAMPLES

In the following illustrative Examples, all parts and percentages are by weight and all temperatures are Centigrade unless otherwise stated. All reactions used commercial HF containing only trace amounts of water.

GENERAL PROCEDURE FOR FLUORINATION

The reactor (a 0.5 inch ID, 12 inch long Inconel pipe) was charged with the amount of dried catalyst as described in the following Examples, and placed in a sand bath. The bath was gradually heated to 400° while nitrogen gas at a flow rate of 50 ml/minute was passed through the reactor to remove traces of water. The temperature was lowered and maintained at about 200° while HF and nitrogen gas (1:4 molar ratio) were passed through the reactor and the nitrogen flow was decreased with time until neat HF was being passed through the reactor. At this point, the temperature was gradually raised to 450° and maintained there for 15 to 300 minutes.

The initial fluorine content of the catalyst composition can be determined to correspond to an $AlF_3$ content, exclusive of the metal, of at least 90%. This determination is based on and the following calculation related to this reaction:

$$Al_2O_3 + 6HF \rightarrow 2AlF_3 + 3H_2O$$

y = weight of unfluorinated catalyst composition which has been dried at a temperature at least 400° C. for at least four hours in a stream of dry nitrogen, air, or other suitable inert medium, minus the weight of metal compound which is in the unfluorinated dried catalyst composition.

z = weight of the fluorinated catalyst composition minus the weight of metal compound calculated as metal fluoride.

Let
x = weight of $Al_2O_3$ remaining after fluorination
y − x = weight of reacted $Al_2O_3$
z − x = weight of $AlF_3$ in the fluorinated catalyst composition $$(y-x)168/102 = z-x$$

Weight of $AlF_3$ as % of dry fluorinated alumina can then be calculated as follows:

$$\frac{(z-x)}{z} \cdot 100\%$$

The temperature was then decreased to the indicated values and, thereafter, $CCl_2$=CHCl flow was started. The flows of HF and $CCl_2$=CHCl were adjusted to give the molar ratio of 2/1 except where otherwise noted and contact times as indicated in the Examples.

The reactor effluent was scrubbed with aqueous potassium hydroxide to remove HCl and HF and sampled on-line with a Hewlett Packard HP 5890 gas chromatograph using a 20 foot long, one-eighth inch diameter, column containing "Krytox" perfluorinated polyether on an inert support and a helium flow of 35 cc/minute. Gas chromatographic conditions were 70° for 3 minutes followed by temperature programming to 180° at a rate of 6°/minute.

EXAMPLES 1-3

The General Procedure for Fluorination was followed using 12.9 g. (20 cc) of $Al_2O_3/MgO$ (3:1) in granular form. The results of the reaction of HF with $CCl_2$=CHCl over the prepared catalyst are given in Table 1.

TABLE 1

|  | Example | | |
|---|---|---|---|
|  | 1 | 2 | 3 |
| Temp., °C. | 125 | 125 | 150 |
| Contact Time, sec. | 10 | 30 | 30 |
| Conversion, % | 12.2 | 18.8 | 12.0 |
|  | Area Percent | | |
| $CF_2ClCH_2Cl$ | 32.0 | 41.5 | 68.3 |
| $CFCl_2CH_2Cl$ | 60.7 | 53.2 | 22.5 |
| $CF_3CH_2Cl$ | 0.8 | 1.1 | 4.2 |

EXAMPLES 4-6

The General Procedure for Fluorination was followed using 19.8 g. (30 cc) of $NiCl_2/Al_2O_3$ (2% Ni) in the form of extrudates one-twentieth inch long. The results of the reaction of HF with $CCl_2$=CHCl over the prepared catalyst are given in Table 2.

TABLE 2

|  | Example | | |
|---|---|---|---|
|  | 4 | 5 | 6 |
| Temp., °C. | 180 | 180 | 160 |
| HF/CHCl = $CCl_2$ mol ratio | 4/1 | 4/1 | 4/1 |
| Contact Time, sec. | 60 | 30 | 30 |
| Conversion, % | 21.6 | 14.0 | 11.6 |
|  | Area Percent | | |
| $CF_2ClCH_2Cl$ | 66.2 | 67.9 | 37.1 |
| $CFCl_2CH_2Cl$ | 6.9 | 18.6 | 49.1 |
| $CF_3CH_2Cl$ | 21.6 | 6.4 | 0.9 |

EXAMPLES 7-8

The General Procedure for Fluorination was followed using 19.5 g. (30 cc) of $MnCl_2/Al_2O_3$ (1.87% Mn) in the form of extrudates one-twentieth inch long. The results of the reaction of HF with $CCl_2$=CHCl over the prepared catalyst are given in Table 3.

TABLE 3

|  | Example | |
|---|---|---|
|  | 7 | 8 |
| Temp., °C. | 150 | 130 |
| HF/CHCl = $CCl_2$ mol ratio | 1/1 | 1/1 |
| Contact Time, sec. | 30 | 60 |
| Conversion, % | 23.1 | 19.5 |
|  | Area Percent | |
| $CF_2ClCH_2Cl$ | 83.1 | 81.5 |
| $CFCl_2CH_2Cl$ | 0.9 | 11.8 |
| $CF_3CH_2Cl$ | 9.5 | 2.6 |

EXAMPLE 9

The General Procedure for Fluorination was followed using 19.68 g. (30 cc) of $FeCl_3/Al_2O_3$ (1.8% Fe) in the form of extrudates one-twentieth inch long. The results of the reaction of HF with $CCl_2$=CHCl over the prepared catalyst are given in Table 4.

TABLE 4

|  | Example 9 |
|---|---|
| Temp., °C. | 150 |
| Contact Time, sec. | 30 |
| Conversion, % | 20.5 |
|  | Area Percent |
| $CF_2ClCH_2Cl$ | 69.0 |
| $CFCl_2CH_2Cl$ | 24.9 |
| $CF_3CH_2Cl$ | 1.8 |

We claim:

1. A process for the preparation of 1,1-difluoro-1,2-dichloroethane and/or 1-fluoro-1,1,2-trichloroethane by fluorination of a trihaloethylene, CClX=CHCl, wherein X=Cl or F, and/or tetrahaloethane, $CCl_2XCH_2Cl$, wherein X=Cl or F, which process comprises contacting in the gaseous phase at about 100° to about 200° C. said trihaloethylene and/or tetrahaloethane with HF and a catalyst composition comprising a catalytically effective amount of at least one metal in an oxidation state greater than zero, said metal selected from the group consisting of iron, manganese, magnesium, and nickel, said metal in combination with an aluminum-containing compound consisting essentially of aluminum and fluorine in such proportions that the fluorine content corresponds to an $AlF_3$ content of at least 90% by weight of the catalyst composition exclusive of the metal, said $AlF_3$ content being obtained by pretreatment of the unfluorinated catalyst composition with a vaporizable fluorine-containing compound, said contacting step producing a product stream containing 1,1-difluoro-1,2-dichloroethane and/or 1-fluoro-1,1,2-trichloroethane, and, thereafter, separating the 1,1-difluoro-1,2-dichloroethane and/or 1-fluoro-1,1,2-trichloroethane from the product stream.

2. The process of claim 1 wherein the contacting step is conducted with said trihaloethylene.

3. The process of claim 2 wherein the said trihaloethylene is trichloroethylene.

4. The process of claim 1 wherein the catalytically effective amount of metal, expressed as the divalent oxide, is about 0.02 to about 50 weight percent of the catalyst composition.

5. The process of claim 4 wherein the catalytically effective amount of metal, expressed as the divalent oxide, is about 0.1 to about 10 weight percent of the catalyst composition.

6. The process as in claims 2, 3, 4 or 5 wherein the HF is contacted with the trihaloethylene at a mol ratio of about 0.5/1 to about 15/1, at a temperature of about 100° to about 180° C. and a contact time of about 2 to about 80 seconds.

7. The process of claim 1 wherein the metal is selected from the group consisting of manganese, nickel, and iron.

8. The process of claim 7 wherein the metal is manganese.

9. The process of claim 1 further comprising the step of recycling at least a portion of the starting materials and underfluorinated products.

10. The process of claim 1 wherein the vaporizable fluorine-containing compound is selected from the group consisting of HF, $SF_4$, $CCl_3F$, $CCl_2F_2$, $CHF_3$ and $CCl_2FCClF_2$.

* * * * *